United States Patent [19]
Austel et al.

[11] 4,026,891
[45] May 31, 1977

[54] 5- OR 6-PYRIDAZINYL-BENZIMIDAZOLES AND SALTS THEREOF

[75] Inventors: Volkhard Austel; Eberhard Kutter, both of Biberach an der Riss; Joachim Heider, Warthausen-Oberhofen; Wolfgang Eberlein, Biberach-Mettenberg; Rudolf Kadatz, Biberach an der Riss; Willi Diederen, Rissegg, all of Germany

[73] Assignee: Boehringer Ingelheim GmbH, Ingelheim am Rhein, Germany

[22] Filed: June 4, 1975

[21] Appl. No.: 583,641

[30] Foreign Application Priority Data
June 10, 1974 Germany ................. 2427943
Apr. 12, 1975 Germany ................. 2516040

[52] U.S. Cl. .................. 260/250 AH; 260/250 A; 260/247.5 D; 260/247.1 L; 424/250; 424/248.5; 424/248.52; 424/248.56; 424/248.57; 424/248.58; 424/248.4
[51] Int. Cl.² ........................ C07D 403/04
[58] Field of Search ............ 260/250 A, 250 AH; 424/250

[56] References Cited
UNITED STATES PATENTS

| | | | |
|---|---|---|---|
| 3,658,827 | 4/1972 | Bezou | 260/250 BN |
| 3,705,157 | 12/1972 | Wiegand et al. | 260/250 AH |
| 3,935,209 | 1/1976 | Beard et al. | 260/250 A |
| 3,969,526 | 7/1976 | Gyurik et al. | 260/250 A |

FOREIGN PATENTS OR APPLICATIONS 272,922  11/1964  Australia .................... 260/250 BN

*Primary Examiner*—Donald G. Daus
*Assistant Examiner*—Mark L. Berch
*Attorney, Agent, or Firm*—Hammond & Littell

[57] ABSTRACT

Compounds of the formula

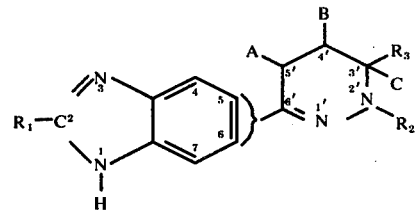

wherein
$R_1$ is hydrogen, trifluoromethyl, alkyl of 1 to 5 carbon atoms, mercapto, lower alkyl-mercapto, phenyl, fluoro-phenyl, tolyl, hydroxy-phenyl, methylmercapto-phenyl, methylsulfinyl-phenyl, methylsulfonyl-phenyl, dimethylamino-phenyl, or mono-, di- or tri-methoxy-substituted phenyl;
A is hydrogen or, together with B, a double bond,
B is hydrogen, alkyl of 1 to 3 carbon atoms or, together with A, a double bond;
C is, together with $R_2$, a double bond, or, together with $R_3$, oxygen;
$R_2$ is hydrogen, alkyl of 1 to 3 carbon atoms or, together with C, a double bond; and
$R_3$ is chlorine, methylamino, morpholino, 4-methylpiperazino or, when $R_2$ is hydrogen or alkyl of 1 to 3 carbon atoms, together with C, oxygen;
and non-toxic, pharmacologically acceptable acid addition salts thereof; the compounds as well as the salts are useful as hypotensives, antithrombotics and cardiotonics.

11 Claims, No Drawings

5- OR 6-PYRIDAZINYL-BENZIMIDAZOLES AND SALTS THEREOF

This invention relates to novel pyridazinyl-substituted benzimidazoles and acid addition salts thereof, as well as to methods of preparing these compounds.

More particularly, the present invention relates to a novel class of pyridazinyl-substituted benzimidazoles represented by the formula (I)

wherein $R_1$ is hydrogen, trifluoromethyl, alkyl of 1 to 5 carbon atoms, mercapto, lower alkyl-mercapto, phenyl, fluoro-phenyl, tolyl, hydroxy-phenyl, methylmercapto-phenyl, methylsulfinyl-phenyl, methylsulfonyl-phenyl, dimethylamino-phenyl or mono-, di- or tri-methoxy-substituted phenyl;

A is hydrogen or, together with B, a double bond,

B is hydrogen, alkyl of 1 to 3 carbon atoms or, together with A, a double bond;

C is, together with $R_2$, a double bond, or, together with $R_3$, oxygen;

$R_2$ is hydrogen, alkyl of 1 to 3 carbon atoms, or, together with C, a double bond; and $R_3$ is chlorine, methylamino, morpholino, 4-methyl-piperazino or, when $R_2$ is hydrogen or alkyl of 1 to 3 carbon atoms, together with C, oxygen;

and non-toxic, pharmacologically acceptable acid addition salts thereof.

The compounds embraced by formula I above may be prepared as follows:

Method A

1. For the preparation of a compound of the formula I wherein $R_3$ and C together are oxygen, by reacting a compound of the formula (II)

wherein A, B and $R_2$ have the same meanings as in formula I, with a carboxylic acid of the formula $$R_1 - COOH \quad (III)$$

wherein $R_1$ has the same meanings as in formula I, or with a functional derivative of the said carboxylic acid.

Examples of suitable functional derivatives are the following: The corresponding azide or nitrile; esters, such as the methyl, ethyl, phenyl or nitrophenyl ester; orthoesters; amides, such as the methyl or dimethyl amide, morpholide, anilide, N-methyl-anilide or imidazolide; amidines; imido esters; thiocarboxylic acid ester, such as the methylthio or phenylthio ester; thiocarboxylic acid amides and S-alkyl-derivatives thereof; acid halides; carboxylic acid anhydrides; dithiocarboxylic acids; dithiocarboxylic acid esters and S-alkyl derivatives thereof.

The reaction is advantageously carried out in the presence of a solvent, such as chlorobenzene, glycol, dimethyl sulfoxide, dimethylformamide or tetrahydronaphthalene, or preferably in the presence of an excess of the compound of the formula III, at elevated temperatures, for instance, at temperatures between 80° and 250° C, optionally in the presence of a condensation agent, such as phosphorus oxychloride, an acid such as sulfuric acid, phosphoric acid or polyphosphoric acid, or optionally in the presence of a base, such as potassium-tert.butylate, sodium hydroxide or triethylamine. The reaction may, however, also be carried out in the absence of a solvent.

2. A 3'-oxo-compound of the formula I may also be obtained by reducing a compound of the formula (IIa)

or (IIb)

wherein A, B, $R_1$ and $R_2$ have the same meanings as in formula I, for instance with hydrogen in the presence of a catalyst, such as Raney nickel, platinum, platinum dioxide or palladized charcoal, or of a metal, such as iron, tin or zinc, or of a metal salt, such as iron(II), tin(II) or chromium(II) salts, to form the corresponding monoacylated diamino compound; optionally isolating the said monoacylated diamino compound from the reaction mixture; and subsequently cyclizing the same by heating it to a temperature between 80° and 250° C, for example, optionally in the presence of an acid, such as hydrochloric acid, sulfuric acid, phosphoric acid or acetic acid, optionally by means of a condensation agent, such as phosphorus oxychloride, or in the presence of a base, and optionally in the presence of a solvent, such as glycol, dimethylformamide, dimethylsulfoxide or chlorobenzene.

Method B

For the preparation of a compound of the formula I wherein $R_3$ and C together are oxygen, by reacting a compound of the formula

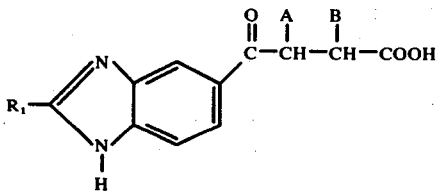

wherein A, B and $R_1$ have the meanings previously defined, or an ester thereof, with a compound of the formula

wherein $R_2$ has the meanings previously defined.

The reaction is preferably carried out in the presence of a solvent, such as glacial acetic acid, ethanol, isopropanol or an excess of the compound of the formula V, at elevated temperatures, for example at temperatures between 50° and 150° C. The reaction may, however, also be carried out in the absence of a solvent.

A compound of the formula I, wherein C and $R_3$ together are oxygen, obtained by method A or B may, if desired, subsequently be converted into the corresponding 3'-halo-substituted compound, for instance, by heating it with the corresponding phosphorus oxyhalide, phosphorus pentahalide or thionyl chloride to temperatures between 80° and 150° C. A halo-substituted compound thus obtained may subsequently be converted into the corresponding amino-substituted compound, for instance by heating it with a corresponding amine to temperatures between 100° and 250° C, optionally in the presence of a solvent, such as ethanol, isopropanol, glycol, dimethyl sulfoxide or dimethylformamide, or into the corresponding hydroxy-substituted compound by hydrolysis, for example in the presence of hydrochloric acid.

A compound of the formula I, wherein A and B are hydrogen, may, if desired, subsequently be converted by dehydrogenation into a compound of the formula I wherein A and B together form an additional carbon-to-carbon bond. The dehydrogenation may be effected with bromine in glacial acetic acid, phosphorus pentachloride, sodium 3-nitro-benzenesulfonate, chromium trioxide, bromosuccinimide, hydrogen peroxide or sodium nitrite according to known methods.

A compound of the formula I, wherein $R_1$ is methylsulfinyl-phenyl or methylsulfonyl-phenyl, may be obtained by oxidation from the corresponding methyl-mercapto-phenyl compound according to known methods. Methylsulfinyl-substituted compounds are, for example, obtained by oxidation with hydrogen peroxide at room temperature; methylsulfonyl-substituted compounds are obtained by oxidation with hydrogen peroxide at temperatures of about 70° C.

A compound of the formula I, wherein $R_1$ is hydroxyphenyl, may subsequently be methylated. The methylation is advantageously carried out in the presence of a solvent, such as ethanol, with methyl iodide or dimethyl sulfate in the presence of an inorganic base, or with diazomethane, preferably at a temperature between 0° and 25° C.

A compound of the formula I, wherein $R_1$ is mercapto, may be converted into a corresponding alkyl-mercapto-substituted compound with the aid of alkylating agents, such as methyl iodide, dimethyl sulfate, isopropyl bromide or the like, optionally in the presence of a base, such as sodium carbonate, potassium tert.butylate, sodium amide or sodium hydride, and optionally in the presence of a solvent, such as dimethylformamide, dimethyl sulfoxide, ethanol, isopropanol or glycol dimethyl ether.

The compounds embraced by formula I above are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, fumaric acid, succinic acid, lactic acid, citric acid, tartaric acid, maleic acid, 8-chlorotheophylline or the like.

The starting compounds of the formulas II through V needed for methods A and B are either known compounds or may be prepared by methods described in the literature, as illustrated in the examples below.

Since the compounds embraced by formula I may exist in their tautomeric 1H- or 3H-forms, the position of substitution on the benzimidazole ring has been designated as 5(6) in the examples below.

The following examples illustrate the present invention and will enable others skilled in the art to understand it more completely. It should be understood, however, that the invention is not limited solely to the particular examples given below.

EXAMPLE 1

2-Methyl-5(6)-(3'-oxo-4',5'-dihydro-2'H-6'-pyridazinyl)-benzimidazole hydrochloride by method A(2)

*a.*

6-(3'-Nitro-4'-acetylamino-phenyl)-4,5-dihydro-3(2H)-pyridazinone 32.5 gm of 3-(3'-nitro-4'-acetylamino-benzoyl)-propionic acid were added to a solution of 32.5 gm of hydrazine hydrate in 180 ml of glacial acetic acid, and the mixture was heated on a steam bath. After cooling, the precipitate formed thereby was suction-filtered off and washed with ether, yielding the desired compound: m.p. 223° C.

*b.*

2-Methyl-5(6)-(3'-oxo-4',5'-dihydro-2'H-6'-pyridazinyl)-benzimidazole and its hydrochloride A mixture consisting of 25.5 gm of 6-(3'-nitro-4'-acetylamino-phenyl)-4,5-dihydro-3(2H)-pyridazinone, 600 ml of ethanol and 125 ml of glacial acetic acid was hydrogenated at 5 atmospheres of hydrogen and room temperature for 1 hour in the presence of 6.2 gm of palladized charcoal. Thereafter, the mixture was filtered, the filter cake was taken up in boiling water, and the solution was cooled after filtering off the catalyst. The obtained crystals were suction-filtered off, taken up in 250 ml of glacial acetic acid, and the resulting mixture was refluxed for 30 minutes. The glacial acetic acid was partly distilled off, and the free base reaction product which precipitated out upon cooling was suction-filtered off and taken up in methanolic hydrochloric acid after drying. The precipitate which was formed after addition of ether was collected, yielding the hydrochloride of the formula

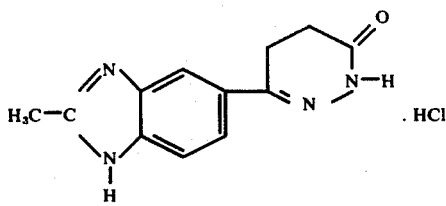

which had a melting point of 334° C.

EXAMPLE 2

2-Methyl-5(6)-(3'-oxo-2'H-6'-pyridazinyl)-benzimidazole hydrochloride

The hot glacial acetic acid solution of 2-methyl-5(6)-(3'-oxo-4',5'-dihydro-2'H-6'-pyridazinyl)-benzimidazole obtained in Example 1b was cooled to 70° C, and 21.8 gm of bromine were added dropwise thereto. The mixture was stirred for 4 hours at 70° C, was then allowed to cool, and the precipitated hydrobromide was suction-filtered off and was converted into the free base with concentrated aqueous ammonia. The base was dissolved in methanolic hydrochloric acid, and the hydrochloride was precipitated with ether; m.p. above 350° C.

Analysis:
Calculated: C-54.98%; H-4.22%; N-21.38%; Cl-13.50%. Found: C-54.70%; H-4.37%; N-21.35%; Cl-13.52%.

EXAMPLE 3

5(6)-(3'-Oxo-4',5'-dihydro-2'H-6'-pyridazinyl)-benzimidazole by method A(1)

a.
6-(4'-Amino-3'-nitro-phenyl)-4,5-dihydro-3(2H)-pyridazinone 18.1 gm of 3-(4-amino-3-nitro-benzoyl)-propionic acid were reacted, as in Example 1a, with 18.1 gm of hydrazine hydrate in 200 ml of glacial acetic acid, yielding the desired compound which had a melting point above 330° C.

b.
6-(3',4'-Diamino-phenyl)-4,5-dihydro-3(2H)-pyridazinone 4.68 gm of 6-(4'-amino-3'-nitro-phenyl)-4,5-dihydro-3(2H)-pyridazinone were hydrogenated in 500 ml of ethanol at 40° C for 4 hours in the presence of 1 gm of platinum dioxide at 5 atmospheres. Thereafter, the solution was cooled and filtered, and the filter cake was boiled with a mixture of 4 parts of isopropanol and 1 part of water. The resulting mixture was filtered, and upon cooling, the desired product crystallized out of the filtrate; m.p. 226° C.

c.
5(6)-(3'-Oxo-4',5'-dihydro-2'H-6'-pyridazinyl)-benzimidazole

A mixture of 2.04 gm of 6-(3',4'-diamino-phenyl)-4,5-dihydro-3(2H)-pyridazinone and 15 ml of formic acid was heated on a steam bath for 1 hour. After distilling off the formic acid, the residue was recrystallized from ethanol/water, yielding the desired end product, m.p. 310° C.

EXAMPLE 4

2-(n-Pentyl)-5(6)-(3'-oxo-4',5'-dihydro-2'H-6'-pyridazinyl)-benzimidazole hydrochloride was prepared analogous to Example 3 from 1.02 gm of 6-(3',4'-diamino-phenyl)-4,5-dihydro-3(2H)-pyridazinone and 10 ml of caproic acid by refluxing. The free base was taken up in ethyl acetate, and the hydrochloride was precipitated with ethereal hydrochloric acid, from which impurities were removed by boiling with acetone; m.p. 298°–300° C.

EXAMPLE 5

2-Trifluoromethyl-5(6)-(3'-oxo-4',5'-dihydro-2'H-6'-pyridazinyl)-benzimidazole was prepared analogous to Example 3 from 2.04 gm of 6-(3',4'-diamino-phenyl)-4,5-dihydro-3(2H)-pyridazinone and 15 ml of trifluoroacetic acid. The residue remaining after distilling off the trifluoroacetic acid was boiled with water and recrystallized from methanol; m.p. 270° C.

Analysis:
Calculated: C-51.02%; H-3.22%; N-19.85%. Found: C-50.80%; H-3.49%; N-19.70%.

EXAMPLE 6

2-(o-Fluoro-phenyl)-5(6)-(3'-oxo-4',5'-dihydro-2'H-6'-pyridazinyl)-benzimidazole and its hydrochloride by method A(2) a.

6-[3'-Nitro-4'-(o-fluoro-benzoylamino)-phenyl]-4,5-dihydro-3(2H)-pyridazinone 11.7 gm of 6-(4'-amino-3'-nitro-phenyl)-4,5-dihydro-3(2H)-pyridazinone were added in small portions to a boiling solution of 15.8 gm of o-fluoro-benzoyl chloride in 350 ml of chlorobenzene, and the resulting mixture was heated for 15 hours more. After cooling, the reaction product was suction-filtered off and boiled with ethanol for purification.

b.
2-(o-Fluoro-phenyl)-5(6)-(3'-oxo-4',5'-dihydro-2'H-6'-pyridazinyl)-benzimidazole hydrochloride 7.12 gm of 6-[3'-nitro-4'-fluoro-benzoylamino)-phenyl]-4,5-dihydro-3(2H)-pyridazinone were hydrogenated in 250 ml of dilute ethanolic hydrochloric acid at 40° C and 5 atmospheres in the presence of 3.5 gm of palladized coal. After filtering off the catalyst, the mixture was evaporated, the residue was digested with water, dried, and taken up in methanolic hydrochloric acid, from which the hydrochloride, m.p. 292° C, was precipitated with ether.

EXAMPLE 7

2-(o,p-Dimethoxy-phenyl)-5(6)-(3'-oxo-4',5'-dihydro-2'H-6'-pyridazinyl)-benzimidazole a. 6-[3'-Nitro-4'-(o,p-dimethoxy-benzoylamino)-phenyl]-4,5-dihydro-3(2H)-pyridazinone was prepared analogous to Example 6a from 13 gm of 6-(4'-amino-3'-nitro-phenyl)-4,5-dihydro-3(2H)-pyridazinone and 22 gm of 2,4-dimethoxy-benzoyl chloride.

b. 2-(o,p-Dimethoxy-phenyl)-5(6)-(3'-oxo-4',5'-dihydro-2'H-6'-pyridazinyl)-benzimidazole was prepared analogous to Example 6b from 6-[3'-nitro-4'-(o,p-dimethoxy-benzoylamino)-phenyl]-4,5-dihydro-3(2H)-pyridazinone. The mixture was filtered, the filter cake was boiled with methanolic aqueous hydrochloric acid, the mixture was filtered while still hot, and the hydrochloride, which precipitated out upon cooling, was converted into the free base, m.p. 240° C, with ammonia.

Analysis:
Calculated: C-65.13%; H-5.18%; N-15.99%.
Found: C-65.10%; H-5.27%; N-15.80%.

EXAMPLE 8

2-Methyl-5(6)-(2'-methyl-3'-oxo-4',5'-dihydro-2'H-6'-pyridazinyl)-benzimidazole and its hydrochloride by method A(2)

a. 2-Methyl-6-(3'-nitro-4'-acetylamino-phenyl)-4,5-dihydro-3(2H)-pyridazinone, m.p. 235° C, was prepared analogous to Example 1a from 3-(3'-nitro-4'-acetylamino-benzoyl)-propionic acid and methylhydrazine.

b.
2-Methyl-6-(3'-amino-4'-acetylamino-phenyl)-4,5-dihydro3(2H)-pyridazinone 3.4 gm of 2-methyl-6-(3'-nitro-4'-acetylamino-phenyl)-4,5-dihydro-3(2H)-pyridazinone were hydrogenated in a mixture of 250 ml of ethanol and 50 ml of glacial acetic acid at 40° C and at a pressure of 5 atmospheres in the presence of 1.5 gm of palladized coal over a period of 30 minutes. Thereafter, the catalyst was filtered off, the filtrate was evaporated, and the residue was triturated with ether and then suction-filtered off.

c.
2-Methyl-5(6)-(2'-methyl-3'-oxo-4',5'-dihydro-2'H-6'-pyridazinyl)-benzimidazole hydrochloride 1.25 gm of the crude 2-methyl-6-(3'-amino-4'-acetylamino-phenyl)-4,5-dihydro-3(2H)-pyridazinone obtained in the preceding step were refluxed with 60 ml of glacial acetic acid. After distilling off the glacial acetic acid, the residue was taken up in ethanol, and the hydrochloride, m.p. 305° C, was precipitated with ethereal hydrochloric acid.

EXAMPLE 9

2-Methyl-5(6)-(3'-chloro-6'-pyridazinyl)-benzimidazole 5 gm of 2-methyl-5(6)-(3'-oxo-2'H-6'-pyridazinyl)-benzimidazole were added in small portions to 250 ml of boiling phosphorus oxychloride, and the mixture was heated for 2.5 hours more. After distilling off the excess phosphorus oxychloride and decomposing the residue with ice water, the insoluble hydrochloride was suction-filtered off and converted into the free base by digesting it with 100 ml of concentrated ammonia; the base was recrystallized from isopropanol/ethanol (10:1), whereupon it had a melting point of 253°–255° C.

EXAMPLE 10

2-Methyl-5(6)-(3'-morpholino-6'-pyridazinyl)-benzimidazole

A mixture of 1.7 gm of 2-methyl-5(6)-(3'-chloro-6'-pyridazinyl)-benzimidazole and 13.1 gm of morphline was heated at 190°–200° C for 16 hours in a closed vessel. The excess of morpholine was then distilled off in vacuo, the residue was triturated with water and then suction filtered off, boiled with water and recrystallized from cyclohexane/isopropanol (2:1). The product still contained 0.5 mol of water of crystallization and had a melting point of 148°–151° C.

EXAMPLE 11

2-Methyl-5(6)-[3'-(N'-methyl-piperazino)-6'-pyridazinyl]benzimidazole, m.p. 145°–148° C, was prepared analogous to Example 10 from 2-methyl-5(6)-(3'-chloro-6'-pyridazinyl)-benzimidazole and N-methyl-piperazine.

EXAMPLE 12

2-Methyl-5(6)-(3'-chloro-6'-pyridazinyl)-benzimidazole 1.32 gm of 2-methyl-5(6)-(3'-oxo-4',5'-dihydro-2'H-6'-pyridazinyl)-benzimidazole hydrochloride were stirred into a solution of 4.2 gm of phosphorus pentachloride in 15 ml of phosphorus oxychloride, and the mixture was refluxed for 7 hours. The phosphorus oxychloride was then distilled off, the residue was treated with ice water, made alkaline with ammonia, suction-filtered off and purified by column chromatography on silicagel (eluant: chloroform/methanol = 9:1), yielding the desired product, which had a melting point of 253°–255° C.

EXAMPLE 13

2-Methyl-5(6)-(3'-oxo-2'H-6'-pyridazinyl)-benzimidazole hydrochloride 0.25 gm of 2-methyl-5(6)-(3'-chloro-6'-pyridazinyl)-benzimidazole were heated with 10 ml of concentrated hydrochloric acid in a closed tube at 120° C for 3 hours. Thereafter, the reaction mixture was made alkaline with ammonia, and the precipitated base was converted into its hydrochloride, as described in Example 2; m.p. above 350° C.

EXAMPLE 14

2-Ethyl-5(6)-(3'-oxo-4',5'-dihydro-2'H-6'-pyridazinyl)-benzimidazole hydrochloride, m.p. 309° C, was prepared analogous to Example 3 from 6-(3',4'-diamino-phenyl)-4,5-dihydro-3(2H)-pyridazinone and propionic acid. The free base was taken up in methanolic hydrochloric acid, and the hydrochloride was precipitated with ether.

EXAMPLE 15

5(6)-(3'-Oxo-2'H-6'-pyridazinyl)-benzimidazole hydrochloride, m.p. above 325° C, was prepared analogous to Example 2 from 5(6)-(3'-oxo-4',5'-dihydro-2'H-6'-pyridazinyl)-benzimidazole.

Analysis:
Calculated: C-53.40%; H-3.64%; N-22.50%; Cl-14.29%.
Found: C-53.00%; H-3.93%; N-22.42%; Cl-14.07%.

EXAMPLE 16

2-Methylmercapto-5(6)-(3'-oxo-4',5'-dihydro-2'H-6'-pyridazinyl)-benzimidazole hydrochloride 4.93 gm of 2-mercapto-5(6)-(3'-oxo-4',5'-dihydro-2'H-6'-pyridazinyl)-benzimidazole were dissolved in 250 ml of dimethylformamide, 1.7 gm of sodium bicarbonate and 2.8 gm of methyl iodide were added to the solution, and the mixture was stirred at room temperature for 1 hour. After addition of another 2.8 gm of methyl iodide, the mixture was stirred at 40°–50° C for one hour more. The mixture was then evaporated to about half its volume, poured into water, and the obtained solid free base product was dissolved in boiling ethanol. The hydrochloride, m.p. above 300° C, was precipitated by addition of ethanolic hydrochloric acid, and recrystallized from ethanol/water.

EXAMPLE 17

The free base 2-isopropylmercapto-5(6)-(3'-oxo-4',5'-dihydro-2'H-6'-pyridazinyl)-benzimidazole, m.p. 224°–227° C (from ethanol), was prepared analogous to Example 16 from the 2-mercapto compound with isopropylbromide and sodium hydride. After pouring into water, the mixture was made alkaline with ammonia.

EXAMPLE 18

5(6)-(2'-Methyl-3'-oxo-4',5'-dihydro-2'H-6'-pyridazinyl)-benzimidazole 1.35 gm of 2-methyl-6-(3',4'-diamino-phenyl)-4,5-dihydro-3(2H)-pyridazinone were refluxed with 10 ml of formic acid for 2 hours. After distilling off the excess formic acid, the mixture was extracted with water and recrystallized from isopropanol/cyclohexane; m.p. 200° C.

EXAMPLE 19

2-Trifluoromethyl-5(6)-(2'-methyl-3'-oxo-4',5'-dihydro-2'-H-6'-pyridazinyl)-benzimidazole, m.p. 250° C, was prepared analogous to Example 18 with trifluoroacetic acid. The mixture was purified on silicagel (eluant: first chloroform, then chloroform/ethanol = 15:1) and recrystallized from isopropanol.

EXAMPLE 20

2-Isopropyl-5(6)-(3'-oxo-4',5'-dihydro-2'H-6'-pyridazinyl)-benzimidazole by method B a.
4-(3-Amino-4-isobutyrylamino-phenyl)-4-oxo-butyric acid methyl ester 15.5 gm of 4-(3'-nitro-4'-isobutyrylamino-phenyl)-4-oxo-butyric acid methyl ester were hydrogenated with 4 gm of palladized coal in 480 ml of ethanol at room temperature and 5 atmospheres pressure. The mixture was then suction-filtered, the filter cake was taken up in hot ethanol, the mixture was filtered, and the reaction product was allowed to crystallize out of the filtrate; m.p. 178° C.

b.
2-Isopropyl-5(6)-(3'-ethoxycarbonyl-1'-oxo-1'-propyl)-benzimidazole hydrochloride 7 gm of 4-(3'-amino-4'-isobutyrylamino-phenyl)-4-oxo-butyric acid methyl ester were refluxed with 100 ml of ethanolic hydrochloric acid for 1 hour. After cooling, the product was precipitated with ether and used in the next step without further purification.

c.
2-Isopropyl-5(6)-(3'-oxo-4',5'-dihydro-2'H-6'-pyridazinyl)-benzimidazole

A mixture of 2 gm of 2-isopropyl-5(6)-(3'-ethoxycarbonyl-1'-oxo-1'-propyl)-benzimidazole hydrochloride, 10 gm of hydrazine hydrate and 10 ml of isopropanol was refluxed for ½ hour. After distilling off the isopropanol, the residue was boiled with water, the insoluble part was filtered off, and the product which separated out of the filtrate after cooling was boiled with acetone; m.p. 230° C.

EXAMPLE 21

2-Methyl-5(6)-(4'-methyl-3'-oxo-4',5'-dihydro-2'H-6'-pyridazinyl)-benzimidazole a.
4-Methyl-6-(3'-amino-4'-acetamino-phenyl)-4,5-dihydro-3(2H)-pyridazinone 2.9 gm of 4-methyl-6-(3'-nitro-4'-acetamino-phenyl)-4,5-dihydro-3(2H)-pyridazinone were hydrogenated in 80 ml of ethanol and 20 ml of glacial acetic acid at room temperature and 5 atmospheres in the presence of 1.5 gm of palladized coal. The catalyst was then filtered off, the filtrate was evaporated, and the residue was used as such in the next step.

b.
2-Methyl-5(6)-(4'-methyl-3'-oxo-4',5'-dihydro-2'H-6'-pyridazinyl)-benzimidazole The raw product obtained in (a) was refluxed in 80 ml of glacial acetic acid for ½ hour, the reaction mixture was poured on ice, and the aqueous mixture was made alkaline with ammonia. The precipitated product was recrystallized from ethanol; m.p. 278°–280° C.

EXAMPLE 22

2-Mercapto-5(6)-(3'-oxo-4',5'-dihydro-2'H-6'-pyridazinyl)-benzimidazole 2 gm of 6-(3',4'-diamino-phenyl)-4,5-dihydro-3(2H)-pyridazinone and 0.87 gm of carbon disulfide were added to a solution of 0.63 gm of potassium hydroxide in 11 ml of 80% ethanol, and the mixture was refluxed for 3 hours. After cooling, 20 ml of water were added, the mixture was acidified with glacial acetic acid, and the precipitate was reprecipitated from dimethylformamide with ice water; m.p. above 300° C.

EXAMPLE 23

2-(p-Methoxy-phenyl)-5(6)-3'-oxo-4',5'-dihydro-2'H-6'-pyridazinyl)-benzimidazole by method B a.
2-(4-Methoxy-phenyl)-5(6)-(3'-ethoxycarbonyl-1'-oxo-1'-propyl)-benzimidazole hydrochloride 22 gm of 4-[3-nitro-4-(p-methoxy-benzoylamino)-phenyl]-4-oxo-butyric acid methyl ester were hydrogenated in 500 ml of ethanol at room temperature and 5 atmospheres in the presence of 5 gm of palladized coal for 1¾ hours. The precipitated mixture of catalyst and 4-[3-amino-4-(p-methoxy-benzylamino)-phenyl]-4-oxo-butyric acid methyl ester was suspended in 1600 ml of ethanol, and the suspension was refluxed for 1 hour while gaseous hydrogen chloride was introduced. The catalyst was filtered off, and the reaction product was precipitated from the filtrate with ether; m.p. 240° C.

b.
2-(4-Methoxy-phenyl)-5(6)-(3'-oxo-4',5'-dihydro-2'H-6'-pyridazinyl)-benzimidazole 12.6 gm of 2-(p-methoxy-phenyl)-5(6)-(3'-ethoxycarbonyl-1'-oxo-1'-propyl)-benzimidazole hydrochloride were refluxed in a mixture of 50 ml of isopropanol and 25 gm of 80% hydrazine hydrate for ½ hour. The crystalline precipitate which remained after distilling off the isopropanol was washed with cold isopropanol and boiled with water; m.p. 174° C.

EXAMPLE 24

2-(o,p-Dimethoxy-phenyl)-5(6)-(3'-oxo-2'H-6'-pyridazinyl)benzimidazole

A solution of 4.2 gm of 2-(o,p-dimethoxy-phenyl)-5(6)-(3'-oxo-4',5'-dihydro-2'H-6'-pyridazinyl)-benzimidazole and 2.22 gm of sodium 3-nitro-benzenesulfonate in 45 ml of 1 N sodium hydroxide was heated at 100° C for 3 hours; then, another 0.5 gm of sodium 3-nitro-benzenesulfonate and 30 ml of 2 N sodium hydroxide were added, and the mixture was again heated at 100° C for 3 hours. After cooling, the mixture was neutralized with hydrochloric acid. The precipitated product was taken up in methanolic ammonia, precipitated with water, dried and extracted and acetone/ether; m.p. 263° C.

EXAMPLE 25

2-(4-Methoxy-phenyl)-5(6)-(3'-oxo-2'H-6'-pyridazinyl)-benzimidazole, m.p. 281° C, was prepared analogous to Example 24 from 2-(p-methoxy-phenyl)-5(6)-(3'-oxo-4', 5'-dihydro-2'H-6'-pyridazinyl)-benzimidazole.

EXAMPLE 26

2-(p-Methoxy-phenyl)-5(6)-(3'-oxo-2'H-6'-pyridazinyl)-benzimidazole methanesulfonate 0.95 gm of 2-(p-methoxy-phenyl)-5(6)-(3'-oxo-4', 5'-dihydro-2'H-6'-pyridazinyl)-benzimidazole were dissolved in 35 ml of glacial acetic acid at 80° C, and 0.96 gm of bromine were added dropwise to the solution. The mixture was stirred for 3 hours at 80° C, then suction-filtered, the filter cake was dissolved in hot methanolic ammonia, and the reaction product was precipitated with water. After drying, the mixture was taken up in absolute methanol, methanesulfonic acid was added to the solution, and the precipitated methanesulfonate was boiled with acetone; m.p. 338° C.

EXAMPLE 27

2-Phenyl-5(6)-(3'-oxo-4',5'-dihydro-2'H-6'-pyridazinyl)-benzimidazole 2.5 gm of 2-phenyl-5(6)-(3'-ethoxycarbonyl-1'-oxo-1'-propyl)-benzimidazole hydrochloride were dissolved in 70 ml of ethanol, 40 ml of 80% hydrazine hydrate were added to the solution, and the mixture was refluxed for 178 hour. After cooling, the mixture was poured into 400 ml of water, and the precipitated product was suction-filtered off and recrystallized from methanol and a small quantity of water; m.p. 265° C.

EXAMPLE 28

2-(p-Methyl-phenyl)-5(6)-(3'-oxo-4',5'-dihydro-2'H-6'-pyridazinyl)-benzimidazole), m.p. 266° C (from ethyl acetate), was prepared analogous to Example 27 from 2-(p-methyl-phenyl)5(6)-(3'-ethoxycarbonyl-1'-oxo-1'-propyl)-benzimidazole hydrochloride.

EXAMPLE 29

2-(p-Methylmercapto-phenyl)-5(6)-(3'-oxo-4',5'-dihydro-2'H-6'-pyridazinyl)-benzimidazole a.
2-(4-Methylmercapto-phenyl)-5(6)-(3'-methoxycarbonyl-1'-oxo-1'-propyl)-benzimidazole hydrochloride 2.5 gm of 6-[3'-nitro-4'-(p-methylmercapto-benzoylamino)-phenyl]-4,5-dihydro-3(2H)-pyridazinone were reduced to 6-[3'-amino-4'-(p-methylmercapto-benzoylamino)-phenyl]-4,5-dihydro-3(2H)-pyridazinone by hydrogenation in 200 ml of methanolic hydrochloric acid at room temperature and 5 atmospheres in the presence of 2.5 gm of pallaized coal. The product partly precipitated and was suction-filtered off together with the catalyst; another part was obtained by evaporation of the filtrate. Both fractions were combined without separating the catalyst, suspended in 100 ml of methanol, and refluxed for 1½ hours. The still hot mixture was filtered, and the product which crystallized out upon cooling was suction-filtered off, washed with ethanol and ether, dried and used as such in the next step.

b.
2-(p-Methylmercapto-phenyl)-5(6)-(3'-oxo-4',5'-dihydro-2'H-6'-pyridazinyl)-benzimidazole 6.8 gm of 2-(p-methylmercapto-phenyl)-5(6)-(3'-methoxycarbonyl-1'-oxo-1'-propyl)-benzimidazole hydrochloride were refluxed in a mixture of 80 ml of glacial acetic acid and 10 ml of hydrazine hydrate for 1 hour. The mixture was poured on ice, and the precipitated product was purified on silicagel (eluant: chloroform/methanol = 19:1); m.p. 248° C.

EXAMPLE 30

2-(p-Dimethylamino-phenyl)-5(6)-(3'-oxo-4',5'-dihydro-2'H-6'-pyridazinyl)-benzimidazole, m.p. 246°–249° C, was prepared analogous to Example 29 from 6-[3'-nitro-4'-(p-dimethyl-amino-benzoylamino)-phenyl]-4,5-dihydro-3(2H)-pyridazinone. The crude product was precipitated from methanolic ammonia with water.

EXAMPLE 31

2-(3,4,5-Trimethoxy-phenyl)-5(6)-(3'-oxo-4',5'-dihydro-2'H-6'-pyridazinyl)-benzimidazole, m.p. 310° C, was prepared analogous to Example 23b from 2-(3,4,5-trimethoxy-phenyl)-5(6)-(3'-ethoxycarbonyl-1'-oxo-1'-propyl)-benzimidazole hydrochloroide.

EXAMPLE 32

2-(o-Methoxy-phenyl)-5(6)-(3'-oxo-4',5'-dihydro-2'H-6'-pyridazinyl)-benzimidazole hydrochloride, m.p. 263° C, was prepared analogous to Example 27 from 2-(o-methoxy-phenyl)-5(6)-(3'-ethoxycarbonyl-1'-oxo-1'-propyl)-benzimidazole hydrochloride. The hydrochloride was precipitated from ethanol with ethereal hydrochloric acid.

EXAMPLE 33

2-(m,p-Dimethoxy-phenyl)-5(6)-(3'-oxo-4',5'-dihydro-2'H-6'-pyridazinyl)-benzimidazole, m.p. 167° C, was prepared analogous to Example 23b from 2-(m,p-dimethoxy-phenyl)-5(6)-(3'-ethoxycarbonyl-1'-oxo-1'-propyl)-benzimidazole hydrochloride.

EXAMPLE 34

2-(m-Methoxy-phenyl)-5(6)-(3'-oxo-4',5'-dihydro-2'H-6'-pyridazinyl)-benzimidazole 2.0 gm of 2-(m-methoxy-phenyl)-5(6)-(3'-ethoxycarbonyl-1'-oxo-1'-propyl)-benzimidazole hydrochloride were refluxed with 10 ml of 80% hydrazine hydrate for 10 minutes. Subsequently, the mixture was diluted with water, and the precipitate formed thereby was recrystallized from acetone; m.p. 260° C.

EXAMPLE 35

2-(o,p-Dimethoxy-phenyl)-5(6)-(4'-methyl-3'-oxo-4',5'-dihydro-2'H-6'-pyridazinyl)-benzimidazole hydrochloride, m.p. 257°-260° C, was prepared analogous to Example 27 from 2-(o,p-dimethoxy-phenyl)-5(6)-(3'-ethoxycarbonyl-1'-oxo-1'-butyl)-benzimidazole hydrochloride. The hydrochloride was precipitated from chloroform/methanol (1:1) with ethereal hydrochloric acid.

EXAMPLE 36

2-(p-Methoxy-phenol)-5(6)-(4'-methyl-3'-oxo-4',5'-dihydro-2'H-6'-pyridazinyl)-benzimidazole, m.p. 140°–150° C, was prepared analogous to Example 29b from 2-(p-methoxy-phenyl)-5(6)-(3'-methoxycarbonyl-1'-oxo-1'-butyl)-benzimidazole hydrochloride. The product was purified by column chromatography (silicagel, chloroform/methanol=50:1 to 19:1), taken up in ethanol and precipitated with water.

EXAMPLE 37

2-(p-Methoxy-phenyl)-5(6)-(2'-methyl-3'-oxo-4',5'-dihydro4'H-6'-pyridazinyl)-benzimidazole, m.p. 90° C (from isopropanol/cyclohexane=2:1), was prepared analogous to Example 23b from 2-(p-methoxy-phenyl)-5(6)-(3'-ethoxycarbonyl-1'-oxo-1'-propyl)-benzimidazole hydrochloride and methyl hydrazine.

EXAMPLE 38

2-(o-Methoxy-phenyl)-5(6)-(2'-methyl-3'-oxo-4',5'-dihydro-2'H-6'-pyridazinyl)-benzimidazole hydrochloride, m.p. 282°–284° C, was prepared analogous to Example 37 from 2-(o-methoxy -phenyl)-5(6)-(3'-ethoxycarbonyl-1'-oxo-1'-propyl)-benzimidazole hydrochloride. The hydrochloride was precipitated from isopropanol with ethereal hydrochloric acid.

EXAMPLE 39

2-(o-Fluoro-phenyl)-5(6)-(2'-methyl-3'-oxo-4',5'-dihydro-2'H-6'-pyridazinyl)-benzimidazole hydrochloride, m.p. 322° C, was prepared analogous to Example 37 from 2-(o-fluoro-phenyl)-5(6)-(3'-ethoxycarbonyl-1'-oxo-1'-propyl)-benzimidazole hydrochloride. The hydrochloride was precipitated from methanol with ethereal hydrochloric acid.

EXAMPLE 40

2-(p-Methoxy-phenyl)-5(6)-(2',4'-dimethyl-3'-oxo-4',5'-dihydro-2'H-6'-pyridazinyl)-benzimidazole, m.p. 120°–130° C (from ethanol/water), was prepared analogous to Example 29b from 2-(p-methoxy-phenyl)-5(6)-(3'-methoxycarbonyl-1'-oxo-1'-butyl)-benzimidazole hydrochloride and methyl hydrazine.

EXAMPLE 41

2-(p-Methylsulfinyl-phenyl)-5(6)-(3'-oxo-4',5'-dihydro-2'H-6'-pyridazinyl)-benzimidazole 0.6 gm of 2-(p-methylmercapto-phenyl)-5(6)-(3'-oxo-4',5'-dihydro-2'H-6'-pyridazinyl)-benzimidazole were dissolved in 100 ml of glacial acetic acid, 0.4 gm of 30% hydrogen peroxide were added to the solution, and the mixture was allowed to stand at room temperature for 2 days. The mixture was subsequently poured into 100 ml of ice water, the aqueous mixture was made alkaline with ammonia and extracted with ethyl acetate, and the extract solution was purified on silicagel (eluant: ethyl acetate); m.p. 291° C.

EXAMPLE 42

2-(p-Methylsulfonyl-phenyl)-5(6)-(3'-oxo-4',5'-dihydro-2'H-6'-pyridazinyl)-benzimidazole 1 gm of 2-(p-methylmercapto-phenyl)-5(6)-(3'-oxo-4',5'-dihydro-2'H-6'-pyridazinyl)-benzimidazole was dissolved in 200 ml of glacial acetic acid, 0.6 gm of 30% hydrogen peroxide were added to the solution, and the mixture was heated at 70° C for 6 hours. Thereafter, the reaction mixture was worked up analogous to Example 26; m.p. 280-284' C.

EXAMPLE 43

2-(p-Methoxy-phenyl)-5(6)-(3'-chloro-6'-pyridazinyl)-benzimidazole hydrochloride 5.6 gm of 2-(p-methoxy-phenyl)-5(6)-(3'-oxo-2'H-6'-pyridazinyl)-benzimidazole were refluxed in 400 ml of phosphorus oxychloride for 2 hours. Thereafter, the excess phosphorus oxychloride was distilled off, the residue was decomposed with ice water, and the precipitated product was suction-filtered off; m.p. 232° C.

EXAMPLE 44

2-(p-Methoxy-phenyl)-5(6)-(3'-morpholino-6'-pyridazinyl)-benzimidazole

A mixture of 1 gm of 2-(p-methoxy-phenyl)-5(6)-(3'-chloro-6'-pyridazinyl)-benzimidazole, 10 ml of morpholine and 10 ml of isopropanol was heated at 180° C for 5 hours in a closed vessel. After distilling off the solvent, the residue was boiled with water, suction-filtered off and purified on a silicagel column (eluant: chloroform/methanol = 19:1 to 9:1); m.p. 197° C.

EXAMPLE 45

2-(p-Methoxy-phenyl)-5(6)-(3'-methylamino-6'-pyridazinyl)benzimidazole, m.p. 87° C, was prepared analogous to Example 44. Chloroform/methanol = 19:1 to 1:1 was used as the eluant.

EXAMPLE 46

2-(p-Methoxy-phenyl)-5(6)-(3'-oxo-2'H-6'-pyridazinyl)-benzimidazole

A mixture of 250 mgm of p-methoxy-thiobenzoic acid morpholide, 200 mgm of 6-(3',4'-diamino-phenyl)-3(2H)-pyridazinone and 200 mgm of potassium tert.butylate was melted, taken up in ethanol after 15 minutes, and purified by chromatography on silicagel (eluant: chloroform/methanol = 9:1); m.p. 281° C.

EXAMPLE 47

2-(p-Methoxy-phenyl)-5(6)-(3'-oxo-2'H-6'-pyridazinyl)-benzimidazole

A mixture of 400 mgm of 4-methoxy-thiobenzoic acid morpholide methoiodide, 200 mgm of 6-(3',4'-diamino-phenyl)-3(2H)-pyridazinone and 3 ml of glycol was boiled for 15 minutes. After dilution with water, the mixture was extracted with ethyl acetate, the ethyl acetate phases were evaporated, and the residue was recrystallized from ethanol; m.. 281° C.

EXAMPLE 48

2-(p-Methoxy-phenyl)-5(6)-(3'-oxo-2'H-6'-pyridazinyl)-benzimidazole 150 mgm of 4-methoxy-benzoic acid nitrile and 200 mgm of 6-(3,4-diamino-phenyl)-3-(2H)-pyridazinone were melted together, taken up in ethanol and purified by chromatography on silicagel column (eluant: chloroform/methanol = 9:1); m.p. 281° C.

EXAMPLE 49

2-(p-Methoxy-phenyl)-5(6)-(3'-oxo-2'H-6'-pyridazinyl)-benzimidazole 150 mgm of 4-methoxy-benzoic acid nitrile, 200 mgm of 6-(3',4'-diamino-phenyl)-3(2H)-pyridazinone and 200 mgm of potassium tert.butylate were melted together, taken up in ethanol and purified by chromatography on a silicagel column (eluant: chloroform/methanol = 9:1); m.p. 281° C.

EXAMPLE 50

2-(p-Methoxy-phenyl)-5(6)-(3'-oxo-2'H-6'-pyridazinyl)-benzimidazole

A mixture of 250 mgm of 4-methoxy-benzoic acid phenyl ester and 200 mgm of 6-(3',4'-diamino-phenyl)-3(2H)-pyridazinone was kept in the molten state for 20 minutes, and was then taken up in ethanol and purified by chromatography on silicagel (eluant: chloroform/methanol = 9:1); m.p. 281° C.

EXAMPLE 51

2-(p-Methoxy-phenyl)-5(6)-(3'-oxo-2'H-6'-pyridazinyl)-benzimidazole 200 mgm of p-methoxy-benzamidine hydrochloride and 200 mgm of 6-(3,4-diamino-phenyl)-3(2H)-pyridazinone were triturated together, and the mixture was heated at 190°-200° C for 10 minutes. After cooling, the mixture was taken up in hot ethanolic ammonia, and the reaction product was allowed to crystallize out; m.p. 281° C.

EXAMPLE 52

2-(p-Methoxy-phenyl)-5(6)-(3'-oxo-2'H-6'-pyridazinyl)-benzimidazole 100 mgm of 2-(p-methoxy-phenyl)-5(6)-(3'-oxo-4',-5'-dihydro-2'H-6'-pyridazinyl)-benzimidazole were added in small portions to a mixture of 300 mgm of chromium(VI)oxide and 2 ml of boiling glacial acetic acid. The resulting mixture was poured into water, the aqueous mixture was extracted with ethyl acetate, and the extract was purified on a silicagel column (eluant: chloroform/methanol = 9:1); m.p. 281° C.

EXAMPLE 53

2-(p-Methoxy-phenyl)-5(6)-(3'-oxo-2'-H-6'-pyridazinyl)-benzimidazole 100 mgm of 2-(p-methoxy-phenyl)-5(6)-(3'-oxo-4',-5'-dihydro-2'H-6'-pyridazinyl)-benzimidazole were suspended in 2 ml of chlorobenzene, and the suspension was refluxed for 30 minutes after addition of 100 mgm of N-bromo-succinimide. Then the solvent was evaporated, and the residue was purified by chromatography on silicagel (eluant: chloroform/methanol = 9:1); m.p. 281° C.

EXAMPLE 54

2-(p-Methoxy-phenyl)-5(6)-(3'-oxo-2'H-6'-pyridazinyl)-benzimidazole 100 mgm of 2-(p-methoxy-phenyl)-5(6)-(3'-oxo-4',-5'-dihydro-2'H-6'-pyridazinyl)-benzimidazole were dissolved in 2 ml of glacial acetic acid, 0.2 ml of hydrogen peroxide (30%) was added to the solution, and the mixture was refluxed for 30 minutes. The mixture was then poured into water, extracted with ethyl acetate, the extract was evaporated, and the residue was recrystallized from ethanol; m.p. 281° C.

EXAMPLE 55

2-(p-Methoxy-phenyl)-5(6)-(3'-oxo-2'H-6'-pyridazinyl)-benzimidazole 100 mgm of 2-(p-methoxy-phenyl)-5(6)-(3'-oxo-4',-5'-dihydro-2'H-6'-pyridazinyl)-benzimidazole were dissolved in 2 ml of glacial acetic acid, and the solution was added dropwise to a solution of 100 mgm of sodium nitrite in 2 ml of water. The resulting mixture was heated at 60° C for 15 minutes, diluted with water and worked up in the usual way; m.p. 281° C.

EXAMPLE 56

2-(p-Hydroxy-phenyl)-5(6)-(3'-oxo-4',5'-dihydro-2'H-6'-pyridazinyl)-benzimidazole, m.p. 338° C, was prepared analogous to Example 23b from 2-(p-hydroxy-phenyl)-5(6)-(3'-ethoxycarbonyl-1'-oxo-1'-propyl)-benzimidazole hydrochloride.

EXAMPLE 57

2-(p-Hydroxy-phenyl)-5(6)-(3'-oxo-2'H-6'-pyridazinyl)-benzimidazole, m.p. 252° C, was prepared analogous to Example 24 from 2-(p-hydroxy-phenyl)-5(6)-(3'-oxo-4',5'-dihydro-2'H-6'-pyridazinyl)-benzimidazole.

EXAMPLE 58

2-(p-Methoxy-phenyl)-5(6)-(3'-oxo-2'H-6'-pyridazinyl)-benzimidazole 0.05 gm of 2-(p-hydroxy-phenyl)-5(6)-(3'-oxo-2'H-6'-pyridazinyl)-benzimidazole was added to a solution of 0.025 gm of sodium in 2 ml of ethanol. 0.2 ml of methyl iodide was added, and the mixture was stirred at room temperature for 30 minutes. After evaporation of the solvent, water was added, the mixture was extracted with ethyl acetate, and the extract was purified by column chromatography on silicagel (eluant: chloroform/methanol = 19:1); m.p. 281° C.

EXAMPLE 59

2-(p-Methoxy-phenyl)-5(6)-(3'-oxo-4',5'-dihydro-2'H-6'-pyridazinyl)-benzimidazole, m.p. 174° C, was prepared analogous to Example 58 from 2-(p-hydroxy-phenyl)-5-(6)-(3'-oxo-4',5'-dihydro-2'H-6'-pyridazinyl)-benzimidazole and dimethyl sulfate.

EXAMPLE 60

2-Trifluoromethyl-5(6)-(3'-oxo-2'H-6'-pyridazinyl)-benzimidazole, m.p. 298° C, was prepared analogous to Example 2 from 2-trifluoromethyl-5(6)-(3'-oxo-4',5'-dihydro-2'H-6'-pyridazinyl)-benzimidazole. Recrystallization from methanol.

The compounds of the present invention, that is, those embraced by formula I above and their non-toxic, pharmacologically acceptable acid addition salts, have useful pharmacodynamic properties. More particularly, the compounds of this invention exhibit hypotensive, antithrombotic and cardiotonic activities in warm-blooded animals, such as dogs and guinea pigs.

The above-indicated pharmacological activities were ascertained for the compounds of the present invention by the standard test methods described below, and the tables show the results obtained for a few representative compounds, where A = 2-Methyl-5(6)-(3'-oxo-4',5'-dihydro-2'H-6'-pyridazinyl)-benzimidazole hydrochloride,
B = 2-Methyl-5(6)-(3'-oxo-2'H-6'pyridazinyl)-benzimidazole hydrochloride,
C = 2-(o,p-Dimethoxy-phenyl)-5(6)-(3'-oxo-4',5'-dihydro-2'H-6'-pyridazinyl)-benzimidazole,
D = 2-Methyl-5(6)-(3'-morpholino-6'-pyridazinyl)-benzimidazole,
E = 2-(o-Fluoro-phenyl)-5(6)-(3'-oxo-4',5'-dihydro-2'H-6'-pyridazinyl)-benzimidazole hydrochloride,
F = 2-Trifluoromethyl-5(6)-(3'-oxo-4',5'-dihydro-2'H-6'-pyridazinyl)-benzimidazole,
G = 2-Methyl-5(6)-2'-methyl-3'-oxo-4',5'-dihydro-2'H-6'-pyridazinyl)-benzimidazole hydrochloride,
H = 5(6)-(3'-Oxo-4',5'-dihydro-2'H-6'-pyridazinyl)-benzimidazole,
I = 2-(p-Methoxy-phenyl)-5(6)-(3'oxo-4',5'-dihydro-2'H-6'-pyridazinyl)-benzimidazole and
K = 2-(p-Methoxy-phenyl)-5(6)-(3'-oxo-2'H-6'-pyridazinyl)benzimidazole methanesulfonate.

1. Determination of thrombocyte aggregation inhibiting activity by the method of Born and Cross [see J. Physiol. 170, 397 (1964)]:

The platelet aggregation inhibiting activity was determined in the platelet-rich plasma of healthy human donors. The rate of decline of the optical density of the platelet suspension was measured and recorded photometrically after the addition of commercial collagen containing 1 mgm of collagen fibrils per ml. From the angle of inclination of the density curve, the rate of aggregation was estimated (Vmax). The optical density was taken as the point on the curve where most light was transmitted (O.D.). To provoke maximum aggregation about 0.01 ml of the collagen solution was added to 1 ml of platelet-rich plasma.

The following table shows the results obtained

TABLE I

| Compound | Inhibition in % after addition of $10^{-4}$ mol/l O.D. |
|---|---|
| A | 100% |
| B | 100% |
| D | 89% |
| F | 100% |
| H | 100% |
| I | 100% |

2. Determination of the hypotensive activity:

The hypotensive activity was determined in mongrel dogs of both sexes (body weight between 19 and 26 kg) under chloralose/urethane (54 + 270 mgm/kg i.v.) and nembutal (10 mgm/kg i.v.) anesthesia. After tracheotomy, the animals were attached to a Harvard artificial respirator using normal air. The arterial blood pressure was measured in the arteria femoralis by a Statham pressure transducer P 23 Dc and registered on a Grass polygraph. The compound under investigation was administered in aqueous solution by intravenous injection into the vena saphena.

The following table shows the average values of 3 tests:

TABLE II

| Compound | Dose mgm/kg i.v. | Decrease in blood pressure mm Hg |
|---|---|---|
| A | 0.25 | 7/9 |
|   | 1.00 | 26/38 |
| B | 0.5 | 18/25 |
|   | 1.0 | 33/32 |
| C | 0.25 | 17/44 |
|   | 1.0 | 33/44 |

3. Determination of the positive inotropic (cardiotonic) activity

The positive inotropic activity was determined as the strengthening effect upon the force of contraction of isolated, spontaneously beating auricles of the guinea pig. Freshly isolated auricles were put into a bath of 100 ml of a tyrode solution at a temperature of 30° C. The tyrode solution was infused with carbogen (95% of $O_2$ and 5% of $CO_2$). The spontaneous contractions of the auricles were registered isometrically with a Statham-Force-Displacement-transducer FT 03 C on a Grass polygraph. The auricles were pre-stretched with 1 gm. After an equilibration period of 20-30 minutes the test compound was added at a concentration of $10^{-5}$ gm/ml.

The following table shows the average results obtained, using at least 5 different auricles per compound:

TABLE III

| Compound | Increase in the force of contraction in % |
|---|---|
| A | 30 |
| B | 20 |
| C | 12 |
| E | 15 |
| G | 13 |
| K | 33 |

4. Acute toxicity:

The acute toxicity of the test compounds was determined for screening purposes in white mice after oral administration of a single dose (observation time: 14 days):

| Compound | Acute toxicity |
|---|---|
| D | 250 mgm/kg p.o. (0 out of 5 animals died) |

For pharmaceutical purposes the compounds according to the present invention are administered to warm-blooded animals perorally, parenterally or rectally as active ingredients in customary dosage unit compositions, that is, compositions in dosage units form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.41 to 3.4 mgm/kg body weight, preferably 0.83 to 2.5 mgm/kg body weight.

The following examples illustrate a few pharmaceutical dosage unit compositions comprising a compound of the present invention as an active ingredient, and represent the best modes contemplated of putting the invention into practical use. The parts are parts by weight unless otherwise specified.

EXAMPLE 61

Tablets

The tablet composition is compounded from the following ingredients:

| | | |
|---|---|---|
| 2-(p-Methoxy-phenyl)-5(6)-(3'-oxo-2'H-6'-pyridazinyl)-benzimidazole methanesulfonate | 100.0 | parts |
| Lactose | 50.0 | " |
| Polyvinylpyrrolidone | 5.0 | " |
| Carboxymethyl cellulose | 19.0 | " |
| Magnesium stearate | 1.0 | " |
| Total | 175.0 | parts |

Preparation:

The benzimidazole compound and the lactose are intimately admixed with each other, the mixture is homogeneously moistened with an aqueous solution of the polyvinylpyrrolidone, the moist mass is granulated by passing it through a 1.5 mm-mesh screen, and the granulate is dried at 50° C in a dryer with circulating air. The dry granulate is then passed through a 1 mm-mesh screen, admixed with the remaining ingredients, and the composition is compressed into 175 mgm-tablets in a conventional tablet making machine. Each tablet contains 100 mgm of the benzimidazole compound and is an oral dosage unit composition with effective hypotensive, antithrombotic and cardiotonic action.

EXAMPLE 62

Coated pills

The pill core composition is compounded from the following ingredients:

| | | |
|---|---|---|
| 2-(p-Methoxy-phenyl)-5(6)-(3'-oxo-2'H-6'-pyridazinyl)-benzimidazole methane-sulfonate | 50.0 | parts |
| Corn starch, dry | 20.0 | parts |
| Soluble starch | 2.0 | parts |
| Carboxymethyl cellulose | 7.0 | parts |
| Magnesium stearate | 1.0 | parts |
| Total | 80.0 | parts |

Preparation:

The benzimidazole compound and the corn starch are intimately admixed with each other, the mixture is moistened with an aqueous solution of the soluble starch and then granulated by passing it through a 1 mm-mesh screen, the granulate is dried at 50° C in a dryer with circulating air, again passed through the screen and admixed with the remaining ingredients, and the composition is compressed into 80 mgm-pill cores which are subsequently coated with a thin shell consisting essentially of a mixture of sugar and talcum. The coated pills are finally polished with beeswax. Each coated pill contains 50 mgm of the benzimidazole compound and is an oral dosage unit composition with effective hypotensive, antithrombotic and cardiotonic action.

EXAMPLE 63

Suppositories

The suppository composition is compounded from the following ingredients:

| | | |
|---|---|---|
| 2-(p-Methoxy-phenyl)-5(6)-(3'-oxo-2'H-6'-pyridazinyl)-benzimidazole methane-sulfonate | | 75.0 parts |
| Suppository base (e.g. cocoa butter) | | 1625.0 parts |
| | Total | 1700.0 parts |

Preparation:

The suppository base is melted, the benzimidazole compound is homogeneously blended into the molten mass with the aid of an immersion homogenizer, and 1700 mgm-portions of the composition are poured into cooled suppository molds and allowed to harden therein. EAch suppository contains 75 mgm of the benzimidazole compound and is a rectal dosage unit composition with effective antithrombotic, cardiotonic and hypotensive action.

EXAMPLE 64

Hypodermic solution

The solution is compounded from the following ingredients:

| | | |
|---|---|---|
| 2-(p-Methoxy-phenyl)-5(6)-(3'-oxo-2'H-6'-pyridazinyl)-benzimidazole methane-sulfonate | | 50.0 parts |
| Sorbitol | | 250.0 parts |
| Distilled water | q.s.ad | 5000.0 parts by vol. |

Preparation:

The benzimidazole compound and the sorbitol are dissolved in a sufficient amount of distilled water, the solution is diluted with distilled water to the indicated volume, the solution is filtered until free from suspended particles, and the filtrate is filled into 5 cc-ampules which are subsequently sterilized for 20 minutes at 120° C and sealed. Each ampule contains 50 mgm of the benzimidazole compound, and the contents thereof are an injectable dosage unit composition with effective hypotensive, antithrombotic and cardiotonic action.

EXAMPLE 65

Drop solution

The solution is compounded from the following ingredients:

| | | |
|---|---|---|
| 2-(p-Methoxy-phenyl)-5(6)-(3'-oxo-2'H-6'-pyridazinyl)-benzimidazole methane-sulfonate | 5.0 | parts |
| Methyl p-hydroxy-benzoate | 0.035 | parts |
| Propyl p-hydroxy-benzoate | 0.015 | parts |
| Oil of anise | 0.05 | parts |
| Menthol | 0.06 | parts |
| Saccharin sodium | 1.0 | parts |
| Glycerin | 10.0 | parts |
| Ethanol | 40.0 | parts |

| Distilled water | q.s.ad | 100.0 | parts by vol. |

Preparation:

The p-hydroxy-benzoates are dissolved in the ethanol, and the oil of anise and the menthol are added to the solution. Thereafter, a solution of the benzimidazole compound, the glycerin and the saccharin sodium in the indicated amount of distilled water is added to the ethanolic solution. The resulting mixed solution is finally filtered until clear. Each 5 ml of the filtrate contain 25 mgm of the benzimidazole compound and are an oral dosage unit composition with effective hypotensive, antithrombotic and cardiotonic action.

Analogous results are obtained when any one of the other benzimidazole compounds embraced by formula I or a non-toxic, pharmacologically acceptable acid addition salt thereof is substituted for the particular benzimidazole compound in Examples 61 through 65. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

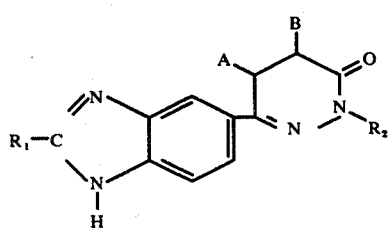

wherein
R₁ is hydrogen, trifluoromethyl, alkyl of 1 to 5 carbon atoms, mercapto, lower alkyl-mercapto, phenyl, fluoro-phenyl, tolyl, hydroxy-phenyl, methylmercapto-phenyl, methylsulfinyl-phenyl, methylsulfonyl-phenyl, dimethylamino-phenyl, or mono-, di- or tri-methoxy-substituted phenyl;
A is hydrogen or, together with B, a double bond;
B is hydrogen, alkyl of 1 to 3 carbon atoms, or together with A, a double bond; and
R₂ is hydrogen or alkyl of 1 to 3 carbon atoms;
or a non-toxic, pharmacologically acceptable acid addition salt thereof.

2. A compound of claim 1,
where R₁ is hydrogen, trifluoromethyl, alkyl of 1 to 5 carbon atoms, fluoro-phenyl, methylmercapto-phenyl, methyl-sulfinyl-phenyl, or mono- or di-methoxy-substituted phenyl;
A is hydrogen, or, together with B, a double bond;
B is hydrogen, methyl or, together with A, a double bond; and
R₂ is hydrogen or methyl;
or a non-toxic, pharmacological acceptable acid addition salt thereof.

3. A compound of claim 1,
where R₁ is methyl, fluoro-phenyl, methoxy-phenyl or dimethoxy-phenyl;
R₂ is hydrogen; and
A and B are each hydrogen or, together with each other, a double bond;
or a non-toxic, pharmacologically acceptable acid addition salt thereof.

4. A compound of claim 3, which is 2-(p-methoxyphenyl)-5(6)-(3'-oxo-4',5'-dihydro-2'H-6'-pyridazinyl)-benzimidazole or a non-toxic, pharmacologically acceptable acid addition salt thereof.

5. A compound of claim 3, which is 2-(p-methoxyphenyl)-5(6)-(3'-oxo-2'H-6'-pyridazinyl)-benzimidazole or a non-toxic, pharmacologically acceptable acid addition salt thereof.

6. A compound of claim 3, which is 2-methyl-5(6)-(3'-oxo-4',5'-dihydro-2'H-6'-pyridazinyl)-benzimidazole or a non-toxic, pharmacologically acceptable acid addition salt thereof.

7. A compound of claim 3, which is 2-methyl-5(6)-(3'-oxo-2'H-6'-pyridazinyl)-benzimidazole or a non-toxic pharmacologically acceptable acid addition salt thereof.

8. A compound of claim 3, which is 2-(o-fluorophenyl)-5(6)-(3'-oxo-4',5'-dihydro-2'H-6'-pyridazinyl)-benzimidazole or a non-toxic, pharmacologically acceptable acid addition salt thereof.

9. A compound of claim 3, which is 2-(o,p-dimethoxy-phenyl)-5(6)-(3'-oxo-4',5'-dihydro-2'H-6'-pyridazinyl)benzimidazole or a non-toxic, pharmacologically acceptable acid addition salt thereof.

10. A pharmaceutical dosage unit composition consisting essentially of an inert pharmaceutical carrier and an effective hypotensive, antithrombotic or cardiotonic amount of a compound of claim 1.

11. The method of lowering the blood pressure, inhibiting thrombocyte aggregation or increasing the force of contraction of the heart muscle in a warm-blooded animal in need of such treatment, which comprises perorally, parenterally or rectally administering to said animal an effective hypotensive, antithrombotic or cardiotonic amount of a compound of claim 1.

* * * * *

UNITED STATES PATENT OFFICE
CERTIFICATE OF CORRECTION

Patent No. 4,026,891             Dated May 31, 1977

Inventor(s) VOLKHARD AUSTEL; EBERHARD KUTTER; JOACHIM HEIDER; WOLFGANG EBERLEIN; RUDOLF KADATZ; WILLI DIEDEREN It is certified that error appears in the above-identified patent and that said Letters Patent are hereby corrected as shown below:

Col. 11, line 57 - "178 hour" should read -- 1/2 hour --

Col. 13, line 36, - "dihydro4'H-6'-" should read

--dihydro-2'H-6'- --

Signed and Sealed this

Fourth Day of October 1977

[SEAL]

Attest:

RUTH C. MASON
Attesting Officer

LUTRELLE F. PARKER
Acting Commissioner of Patents and Trademarks